United States Patent [19]

Stefanska et al.

[11] 4,351,937
[45] Sep. 28, 1982

[54] N-GLYCOSYL DERIVATIVES OF ANTHRACYCLINE ANTIBIOTICS AND THE METHOD OF THEIR PREPARATION

[75] Inventors: Barbara J. Stefańska, Gdańsk-Oliwa; Leonard S. Falkowski, Gdańsk; Edward Borowski, Gdańsk-Wrzeszcz, all of Poland

[73] Assignee: Politechnika Gdanska, Majakowskiego, Poland

[21] Appl. No.: 172,262

[22] Filed: Jul. 25, 1980

[30] Foreign Application Priority Data

Oct. 17, 1979 [PL] Poland .................................. 219049

[51] Int. Cl.³ ............................................. C07H 15/24
[52] U.S. Cl. .................................... 536/6.4; 424/180
[58] Field of Search ...................................... 536/17 A

[56] References Cited

U.S. PATENT DOCUMENTS 4,093,796  6/1978  Falkowski et al. ............... 536/17 R
4,127,714 11/1978  Umezawa et al. ................ 536/17 A
4,169,142  9/1979  Penco et al. ...................... 536/17 A

OTHER PUBLICATIONS

Falkowski et al., "The Journal of Antibiotics", vol. XXVIII, No. 3, pp. 244–245, 1975.

Primary Examiner—Johnnie R. Brown

[57] ABSTRACT

The invention relates to the method of preparation of N-glycosyl compounds of anthracyclin antibiotics of formula I

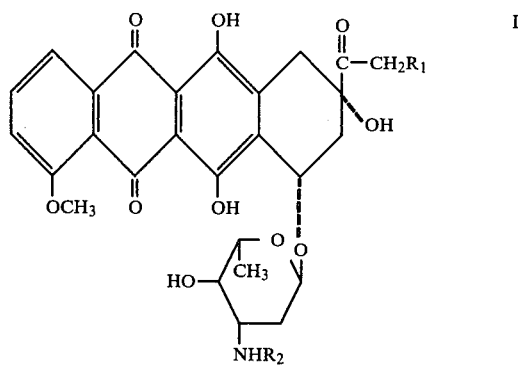

where $R_1$ is the hydrogen atom or hydroxylic group, whereas $R_2$ is the residue of a mono- or oligosaccharide of a series of aldeses and ketoses or the derivatives reacted with the amine group of the antibiotic. The invention depends upon the reaction of the antibiotic, which is converted into the form of base, in an organic solvent by treatment with molar excess of the saccharide or its derivative at temperature from 20° up to 60° C., for several hours, in the presence of a catalyst, under continuous stirring. The product is precipitated from the reaction mixture upon the addition of a nonpolar solvent and subsequently is purified by known methods.

3 Claims, 3 Drawing Figures

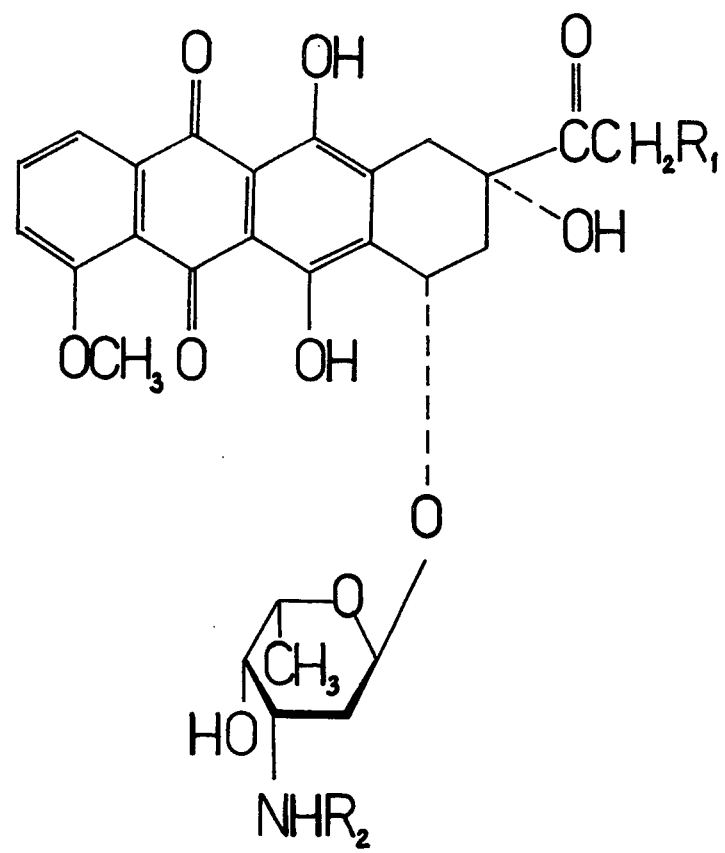
FORMULA 1

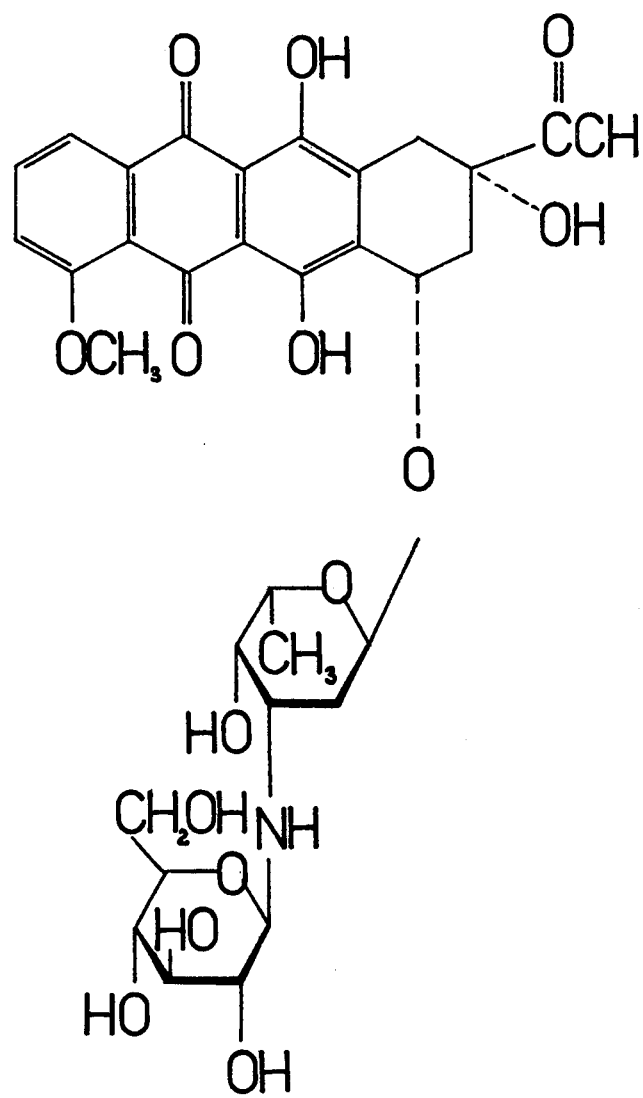
FORMULA 2

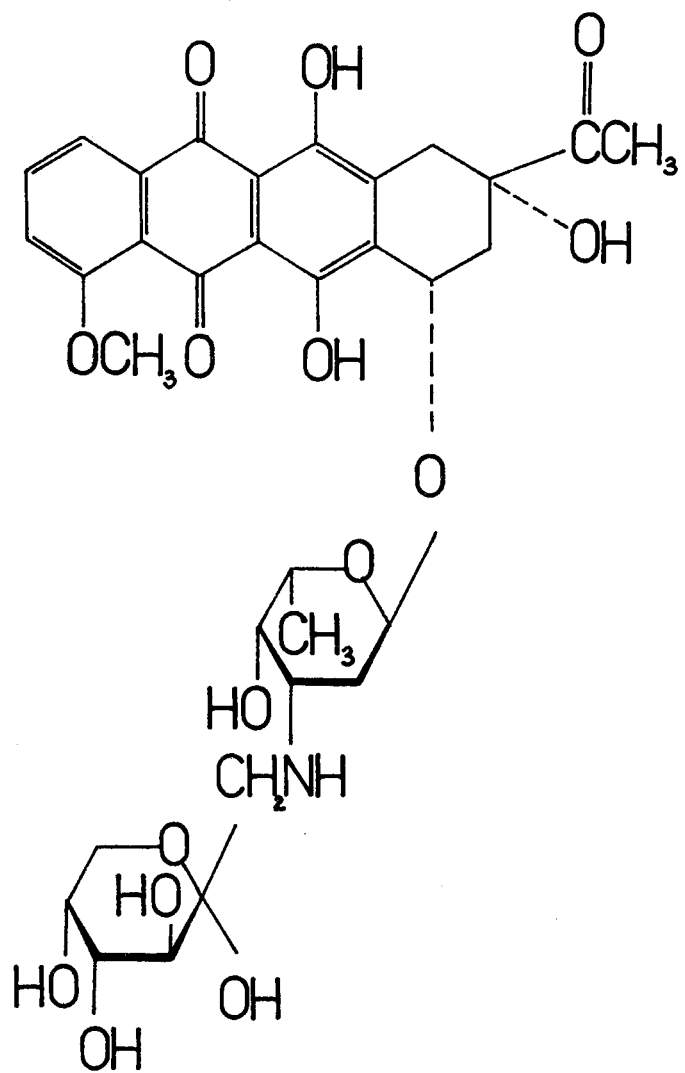
FORMULA 3

N-GLYCOSYL DERIVATIVES OF ANTHRACYCLINE ANTIBIOTICS AND THE METHOD OF THEIR PREPARATION

FIELD OF THE INVENTION

The invention relates to N-glycosyl compounds of the anthracycline antibiotics of formula I where $R_1$ is a hydrogen atom of hydroxyl group, and $R_2$ is the residue of a mono- or oligosaccharide or derivative thereof reacted with the amino group of the antibiotic and the method of their preparation.

BACKGROUND OF THE INVENTION

Known derivatives of anthracycline antibiotics exhibit improved pharmacological properties as compared with the parent antibiotics—F. Arcamone, Canc. Chem. Rep. 1975, 6/No 2/,23. F. Arcamone, J. Med Chem. 1974, p. 17 and 33 s., Proc. of the 11th Intern. Cancer Congress Florence 1974.

The disadvantages of the described compounds as well as the native antibiotics and their structural analogues are their toxicity, particularly cardiotoxicity, and their unstability. These cause lowering of the efficacy of therapy and their solubility in water.

The Invention

The N-glycosyl compounds of anthracycline antibiotics of the formula I,

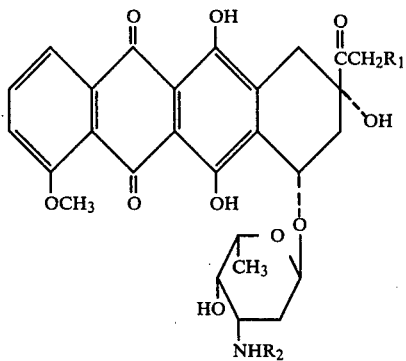

where $R_1$ is a hydrogen atom or hydroxyl group, and $R_2$ is the residue of a mono- or oligosaccharide of a series of aldoses and ketoses and their reaction products reacted with the amino group of the antibiotic.

The method of preparation of the N-glycosyl derivatives of anthracycline antibiotics of formula I, where $R_1$ is the hydrogen atom or hydroxyl group, whereas $R_2$ is the residue of a mono- or oligosaccharide of a series of aldoses and ketoses or their reaction products with the amino group of the antibiotic, according to our invention depends upon the reaction of the antibiotic, converted into the form of its base, in organic solvent by treatment with a molar excess of the saccharide or its ester or amide derivative at temperature from 20° C. up to 60° C., for several hours, in the presence of a catalyst under continuous stirring. The product is precipitated from the reaction mixture upon the addition of a nonpolar solvent and subsequently is purified by known methods.

The anthracycline antibiotics used were daunorubicine (Merck Index #2815) ($R_1$=H) adriamycine (Merck Index #3428) ($R_1$=OH).

The solvents used were N,N-dimethylacetamide and N,N-dimethylformamide.

The saccharides used were glucose, fructose, ribose and the N-octylamide, N-butylamide- and their methyl esters with glucuronic acid. The catalysts used were acetic acid and Lewis acids.

The structure of these obtained derivatives of the anthracycline antibiotics had been determined by means of spectroscopic methods: mass spectrometry, $^1H$ nuclear magnetic resonance, infrared, electronic absorption spectroscopy.

The complete procedure of structure analysis is given below for the product formed in the reaction of daunorubicin with glucose. The performed investigations indicate that the reaction according to our invention yields the target substance which is substituted only at the amino group of the native antibiotic, with the remaining part of its molecule being unchanged. The reaction carried out at neutral conditions yielded N-/glucos-1-yl/ daunorubicin characterized by the formula 2, whereas in the presence of the above mentioned catalysts the Amadori-Heyns rearrangement took place affording N-/1-deoxy-fructos-1-yl/ daunorubicin characterized by the formula 3.

The N-glycosyl derivatives exhibited electronic absorption spectra identical with those of the parent antibiotics. The infrared spectrum of N-deoxyfructosyl derivative displayed an absorption bond at 1720 $cm^{-1}$ of higher intensity as compared with the remaining substances.

The field desorption mass spectrum of N-/N-deoxyfructos-1-yl/ daunorubicin yielded molecular ions at m/z=689 /$M^+$, 100%/ and m/z=671 /M—18.25%/.

The electronic impact mass spectrum of per-O-trimethylsilyl-N-/1-deoxyfructos-1-yl/ daunorubicin revealed significant molecular ions and fragmentation pattern characteristic for N-glycosyl derivatives formed as the result of the Amadori-Heyns rearrangement. The above discussed investigations gave the evidence, that condensation of the amino group of the antibiotic with the saccharide, performed in the presence of the acidic catalyst, yielded a rearrangement product in which the remaining part of the antibiotic molecule remained unchanged.

The field desorption mass spectrum of N-/glucos-1-yl/ daunorubicin exhibited molecular ions at m/z=689 /$M^+$/. The electron impact mass spectrum of hexo-O-trimethylsilyl-N-/glucos-1-yl/ daunorubicin revealed fragmentation pattern characteristic for N-glycosides. This type of derivatives in neutral and acid solutions are less stable than the rearrangement products.

Evidence had been given for the antitumor activity of the N-glycosyl derivatives of anthracycline antibiotics against leukemia L 1210.

The antitumor activity of daunorubicin and its N-glycosyl derivatives against mice leukemia L 1210 is illustrated in the following table:

TABLE 1

| No | Compound tested | daily doze/ mg/kg/ | T/C % |
|---|---|---|---|
| 1. | Daunorubicin | 10 | 130 |
| 2. | N/1-deoxy-fructos-1-yl/daunorubicin | 10 | 130 |
| 3. | N—/glucos-1-yl/ daunorubicin | 20 | 140 | where T/C means the mean time of life.

The CDF mice were inoculated with $10^5$ cells of LK 10 leukemia and the drug was given intraperitioneally five successive days.

The advantages of the anthracycline derivatives according to our invention are their antitumor activities and the simple method of their preparation.

The N-glycosyl derivatives of anthracycline antibiotics and the method of their preparation are presented by the following examples:

EXAMPLE I 0.58 g of daunorubicin hydrochloride was dissolved in 2 ml of water, treated with two molar excess of imidazol and extracted three times with 25 of chloroform-methanol 20:1 mixture. The organic layer was dried over sodium sulphate, filtered and evaporated under reduced pressure at a temperature range of 15°–20° C. The obtained daunorubicin base dissolved in 3 ml of N,N-dimethylacetamide, treated with 0.3 g of glucose and 0.03 ml of acetic acid and stirred 12 hours at 35° C. After completion of the reaction 150 ml of ethyl ether was added, the precipitate centrifuged, washed several times with 5 ml of chloroform and the residue purified by means of chromatography on column with sephadex LH 20 in solvent system methanol-chloroform 5:1. The fractions containing the derivative were concentrated and the N-/1-deoxyfructos-1-yl/ daunorubicin precipitated upon addition of ethyl ether, washed with ethyl ether and dried under reduced pressure. Obtained 0.56 g of the derivative, for 80% of the theoretical yield.

EXAMPLE II 0.53 g of daunorubicin base and 0.3 g of glucose were dissolved in 3 ml of N,N-dimethylformamide and stirred 12 hours at 35° C. After completion of the reaction 150 ml of ethyl ether was added, the precipitate was centrifuged, washed several times with chloroform and the residue purified by means of chromatography on column with Sephadex LH 20 in solvent system chloroform-methanol 5:1. The fractions containing the derivative were concentrated and the N-/glucos-1-yl/ daunorubicin precipitated with ethyl ether, washed with ethyl ether, dried under reduced pressure. Obtained 0.45 g of the derivative, for 60% of the theoretical yield.

EXAMPLE III 0.53 g of daunorubicin base and 0.5 g of glucuronic acid N-octyl amide were dissolved in 5 ml of N,N-dimethylformamide and stirred 12 hours at 35° C. The reaction mixture was further worked up as described in example II. Obtained 0.55 g of N-N'-octylglucuron-1-yl-amid-daunorubicin for 65% of the theoretical yield.

EXAMPLE IV 0.53 g of daunorubicin free base and 0.4 g of glucuronic acid methyl ester were dissolved in 3.4 ml of N,N-dimethylacetamide, containing 0.03 ml of acetic acid and the mixture stirred 12 hours at 35° C. The reaction mixture was further worked up as described in Example I. Obtained 0.5 g of N-/methyl-1-deoxyfructuron-1-yl-ate/ daunorubicin for 70% of the theoretical yield.

EXAMPLE V 0.1 g of adriamycin in the form of free base and 0.3 g of glucose were dissolved in 1 ml of N,N-dimethylacetamide, added was 0.036 ml of acetic and the mixture stirred 12 hours at 35° C. The reaction mixture was further worked up as described in Example I. Obtained 0.5 g of N-/1-deoxyfructos-1-yl/ adriamycin for 70% of the theoretical yield.

EXAMPLE VI 0.53 g of daunorubicin base and 0.3 g of ribose were dissolved in 3 ml of N,N-dimethylacetamide, with 0.03 ml of acetic acid and the mixture stirred 12 hours at 35° C. The reaction mixture was further worked up as described in Example I. Obtained 0.5 g of N-/1-deoxyketo arabinos-1-yl/-daunorubicin, for 70% of the theoretical yield.

EXAMPLE VII 0.1 g of adriamycin base and 0.1 g of glucuronic acid N-butylamide were dissolved in 1 ml of N,N-dimethylacetamide, with 0.006 ml of acetic acid and the mixture stirred 12 hours at 35° C. The reaction mixture was further worked up as described in Example I. Obtained 0.09 g N-N'-butyl-1-deoxy-1-fructuron-1-yl amide/adriamycin for 60% of the theoretical yield.

EXAMPLE VIII 0.53 g of daunorubicin base and 0.4 g of fructose were dissolved in 3 ml of N,N-dimethylacetamide and stirred 24 hours at 25° C. The reaction mixture was further worked up as described in Example I. Obtained 0.4 g N-/2-deoxy-glucos-2-yl/ daunorubicin, for 60% of the theoretical yield.

What we claim is:

1. Anthracycline antibiotics selected from the group consisting of daunorubicin and adriamycin, of the formula

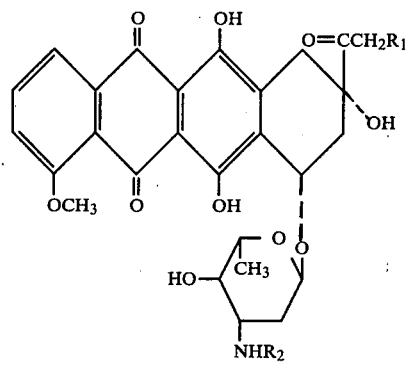

where $R_1$ is hydrogen or a hydroxyl group and where $R_2$ is selected from the group consisting of ribose, glucose, fructose residues and the glucuronamide residues formed with N-octylamide, N-butylamide and the methyl ester of glucuronic acid.

2. The method of preparation of the N-glycosyl compounds of anthracycline antibiotics according to claim 1 of the formula I comprising the steps of reacting the selected anthracycline antibiotic free-base in an organic solvent selected from the group consisting of dimethylacetamide and dimethylformamide with a molar excess of a saccharide or its derivative selected from the group consisting of ribose, glucose, fructose, the glucuronic acid N-octylamide, the glucuronic acid N-butylamide and the glucuronic acid methyl ester; at a temperature from 20° to 60° C., for at least about 12 hours in the presence of an acidic catalyst, under continuous stirring and the product is precipitated from the reaction mixture upon addition of non-polar solvent and subsequently is purified.

3. The method according to claim 2, wherein the catalyst is selected from the group consisting of acetic acid and Lewis acids.